United States Patent
Moon et al.

(10) Patent No.: US 10,716,822 B2
(45) Date of Patent: Jul. 21, 2020

(54) SEED OF NEW SOYBEAN CULTIVAR SCEL-1, PLANT BODY OF THE SEED AND PART OF THE PLANT BODY, AND EXTRACT OBTAINED FROM THE SEED

(71) Applicants: KOREA INSTITUTE OF SCIENCE AND TECHNOLOGY, Seoul (KR); REPUBLIC OF KOREA(MANAGEMENT : RURAL DEVELOPMENT ADMINISTRATION), Jeonju-si, Jeollabuk-do (KR)

(72) Inventors: Jung Kyung Moon, Jeollabuk-do (KR); Man Soo Choi, Changwon-si (KR); Soo Kwon Park, Jeollabuk-do (KR); Nam Hee Jeong, Jeonju-si (KR); Yongsoo Choi, Gangneung-si (KR); Sungdo Ha, Gangneung-si (KR); Cheol-Ho Pan, Gangneung-si (KR); Sung Taeg Kang, Cheonan-si (KR); Soon Chun Jeong, Cheongju-si (KR)

(73) Assignees: KOREA INSTITUTE OF SCIENCE AND TECHNOLOGY, Seoul (KR); REPUBLIC OF KOREA (MANAGEMENT : RURAL DEVELOPMENT ADMINISTRATION), Jeonju-si (KR)

( * ) Notice: Subject to any disclaimer, the term of this patent is extended or adjusted under 35 U.S.C. 154(b) by 0 days.

(21) Appl. No.: 16/212,030

(22) Filed: Dec. 6, 2018

(65) Prior Publication Data

US 2020/0000866 A1 Jan. 2, 2020

(30) Foreign Application Priority Data

Jun. 29, 2018 (KR) ........................ 10-2018-0075957

(51) Int. Cl.
| | | |
|---|---|---|
| A61K 36/00 | (2006.01) | |
| A61K 36/48 | (2006.01) | |
| A61P 39/06 | (2006.01) | |
| A61P 1/16 | (2006.01) | |
| A01H 6/54 | (2018.01) | |
| A01H 5/10 | (2018.01) | |

(52) U.S. Cl.
CPC ............... *A61K 36/48* (2013.01); *A01H 5/10* (2013.01); *A01H 6/542* (2018.05); *A61P 1/16* (2018.01); *A61P 39/06* (2018.01); *A61K 2236/333* (2013.01)

(58) Field of Classification Search
CPC .................................................. A61K 36/00
See application file for complete search history.

(56) References Cited

FOREIGN PATENT DOCUMENTS

| KR | 2006053634 A | * | 5/2006 |
|---|---|---|---|
| KR | 10-2007-0095251 A | | 9/2007 |
| KR | 10-2015-0019569 A | | 2/2015 |
| KR | 10-2015-0053321 A | | 5/2015 |
| KR | 10-1862265 B1 | | 7/2017 |

OTHER PUBLICATIONS

Xu et al, Differences in the metabolic profiles and antioxidant activities of wild and cultivated black soybeans evaluated by correlation analysis. Food research international (Ottawa, Ont.), (20171000) vol. 100, No. Pt 2, pp. 166-174. (Year: 2017).*
Yang et al, Effects of soy protein on alcoholic liver disease in rats undergoing ethanol withdrawal. The Journal of nutritional biochemistry, (Jun. 2012) vol. 23, No. 6, pp. 679-684 (Year: 2012).*
Cha et al., "Comparison of Antioxidant Activity and Composition in Glycine max Merr. and Glycine soja Siebold et Zucc.," Kor. J. Pharmcogn. 27(3), 1996, pp. 190-195.
CHENGJA3, Cultivar Application Publication No. 2005-176, 2005, 1 page.
Guideline, Soybean *Glycine max* (L.) Merrill, 2014, 21 pages.
Wonheug, Cultivar Application Publication No. 2010-341, 2010, 1 page.
Gomes et al., "Four Conventional Soybean [*Glycine max* (L.) Merrill] Seeds Exhibit Different Protein Profiles as Revealed by Proteomic Analysis," J. Agric. Food. Chem. (2014), vol. 62, pp. 1283-1293.
International Search Report dated Mar. 26, 2019, in PCT/KR2018/015455.
Lee et al., "Comprehensive phenolic composition analysis and evaluation of Yak-Kong soybean (*Glycine max*) for the prevention of atherosclerosis," Food Chemistry (2017), vol. 234, pp. 486-493.
Lee et al., "Soybean [*Glycine max* (L.) Merrill]: Importance as a Crop and Pedigree Reconstruction of Korean Varieties," Plant Breed Biotech. (Sep. 2015), vol. 3, No. 3, pp. 179-196.
Written Opinion of the International Searching Authority dated Mar. 26, 2019, in PCT/KR2018/015455.
Extended European Search Report dated May 27, 2019, in European Patent Application No. 18210854.8.
Jung, J.H. and H. S. Kim, "The inhibitory effect of black soybean on hepatic cholesterol accumulation in high cholesterol and high fat diet-induced non-alcoholic fatty liver disease," Food and Chemical Toxicology (2013), vol. 60, pp. 404-412.
Lee et al., "Anthocyanin and Isoflavone Contents in Korean Black Soybean Landraces and Their Antioxidant Activities," Plant Breed. Biotech. (Nov. 2016), vol. 4, No. 4, pp. 441-452.
Xu et al., "Differences in the metabolic profiles and antioxidant activities of wild and cultivated black soybeans evaluated by correlation analysis," Food Research International (2017), vol. 100, pp. 166-174.

* cited by examiner

*Primary Examiner* — Qiuwen Mi
(74) *Attorney, Agent, or Firm* — Birch, Stewart, Kolasch & Birch, LLP

(57) ABSTRACT

Provided are a seed of new soybean cultivar SCEL-1, a plant body of the seed or a part of the plant body, and an extract obtained from the seed.

8 Claims, 4 Drawing Sheets

FIG. 1

| YEAR | 2012 | 2013 | 2014 | 2015 | 2016 | 2017 |
|---|---|---|---|---|---|---|
| | | 1 | 1 | ① | 1 | |
| | | ② | 2 | 2 | 2 | |
| | | · | ③ | 3 | ③ | SCEL-1 |
| | | · | · | · | · | |
| | | · | · | · | · | |
| | | 20 | 20 | 20 | 20 | |
| REMARK | DISTRIBUTION | | QUALIFICATION TEST AND PURE LINE SELECTION | | | YIELD TEST |

SEED OF NEW SOYBEAN CULTIVAR SCEL-1, PLANT BODY OF THE SEED AND PART OF THE PLANT BODY, AND EXTRACT OBTAINED FROM THE SEED

CROSS-REFERENCE TO RELATED APPLICATION

This application claims the benefit of Korean Patent Application No. 10-2018-0075957, filed on Jun. 29, 2018, in the Korean Intellectual Property Office, the disclosure of which is incorporated herein in its entirety by reference.

BACKGROUND

1. Field

One or more embodiments relate to a seed of soybean *Glycine max* (L.) Merrill cultivar SCEL-1, a plant body of the seed and a part of the plant body, a method of producing a product of the plant body or the part of the plant body, and a composition for antioxidation, protection of hepatocytes, or reduction of amounts of total cholesterol, high-density lipoproteins (HDLs), low-density lipoproteins (LDLs), and triglycerides (TGs), the composition including, as an active ingredient, an extract obtained by performing an extraction process on a soybean cultivar seed by using water, $C_1$-$C_6$ alcohol, or a mixture thereof.

2. Description of the Related Art

Soybeans are an abundant crop source of vegetable proteins, and contain not only proteins, but also a variety of excellent functional materials including unsaturated fatty acids, amino acids, isoflavones, and phenolic acids. In this regard, soybeans are being used as a protein source to replace animal proteins.

Researchers, C H A, Baecheon et al. (The Korean Society of Pharmacognosy, Vol. 27(3): pages 190-195 (published in 1996)), discovered that an extract obtained by performing an extraction process (hereinafter referred to as an ethanol extract) on a wild-type soybean *Glycine soja* Siebold et Zucc. by using ethanol contains (−)-epicatechin, unlike an ethanol extract of another soybean *Glycine max* (L.) Merrill. In addition, the researchers also discovered that the ethanol extract of the wild-type soybean has antioxidative activity, but did not disclose that the soybean contains (−)-epicatechin.

Therefore, there is a demand for a new soybean cultivar having excellent antioxidant activity and/or different physiological functions from the known soybeans.

SUMMARY

One or more embodiments include a seed of soybean *Glycine max* (L.) Merrill cultivar SCEL-1, a plant body of the seed and a part of the plant body, and a progeny of the plant body, wherein the seed contains cyanidin-3-O-glucoside, procyanidin B2, and epicatechin, wherein an amount of the procyanidin B2 is greater than that of the cyanidin-3-O-glucoside, and a representative sample of the seed is deposited with the Korean Agricultural Culture Collection (KACC), which is an International Depository Authority (IDA) under the Budapest Treaty on the International Recognition of the Deposit of Microorganisms for the Purpose of Patent Procedure under the accession number KACC 88002BP on Nov. 8, 2018.

One or more embodiments include a soybean plant body obtained by transforming the plant body of the seed or the part of the plant body, a seed from which the soybean plant is obtained, and a progeny of the soybean plant.

One or more embodiments include a method of producing a product of a plant body of a seed or a part of the plant body, the method including obtaining a plant body of a soybean cultivar seed or a part of the plant body; and producing a product from the plant body or the part thereof, wherein the soybean cultivar seed is a seed of soybean *Glycine max* (L.) Merrill cultivar SCEL-1, the seed containing cyanidin-3-O-glucoside, procyanidin B2, and epicatechin, wherein an amount of the procyanidin B2 is greater than that of the cyanidin-3-O-glucoside, and a representative sample of the seed is deposited with the Korean Agricultural Culture Collection (KACC), which is an International Depository Authority (IDA) under the Budapest Treaty on the International Recognition of the Deposit of Microorganisms for the Purpose of Patent Procedure under the accession number KACC 88002BP on Nov. 8, 2018.

One or more embodiments include a composition for antioxidation, protection of hepatocytes, or reduction of amounts of total cholesterol, high-density lipoproteins (HDLs), low-density lipoproteins (LDLs), and triglycerides (TGs), the composition including, as an active ingredient, an extract obtained by performing an extraction process on a soybean cultivar seed by using water, $C_1$-$C_6$ alcohol, or a mixture thereof, wherein the soybean cultivar seed is a seed of soybean *Glycine max* (L.) Merrill cultivar SCEL-1, the seed containing cyanidin-3-O-glucoside, procyanidin B2, and epicatechin, wherein an amount of the procyanidin B2 is greater than that of the cyanidin-3-O-glucoside, and a representative sample of the seed is deposited with the Korean Agricultural Culture Collection (KACC), which is an International Depository Authority (IDA) under the Budapest Treaty on the International Recognition of the Deposit of Microorganisms for the Purpose of Patent Procedure under the accession number KACC 88002BP on Nov. 8, 2018.

One or more embodiments include a composition for antioxidation or protection of hepatocytes, the composition including, as active ingredients, cyanidin-3-O-glucoside or a physiologically acceptable salt thereof, procyanidin B2 or a physiologically acceptable salt thereof, and epicatechin or a physiologically acceptable salt thereof, at a weight ratio of 1:2.0 to 2.1:0.43 to 0.46 on a weight basis, respectively.

BRIEF DESCRIPTION OF THE DRAWINGS

These and/or other aspects will become apparent and more readily appreciated from the following description of the embodiments, taken in conjunction with the accompanying drawings in which:

FIG. 1 shows a schematic breeding diagram of a soybean cultivar according to the present disclosure;

DETAILED DESCRIPTION

Figure 2:
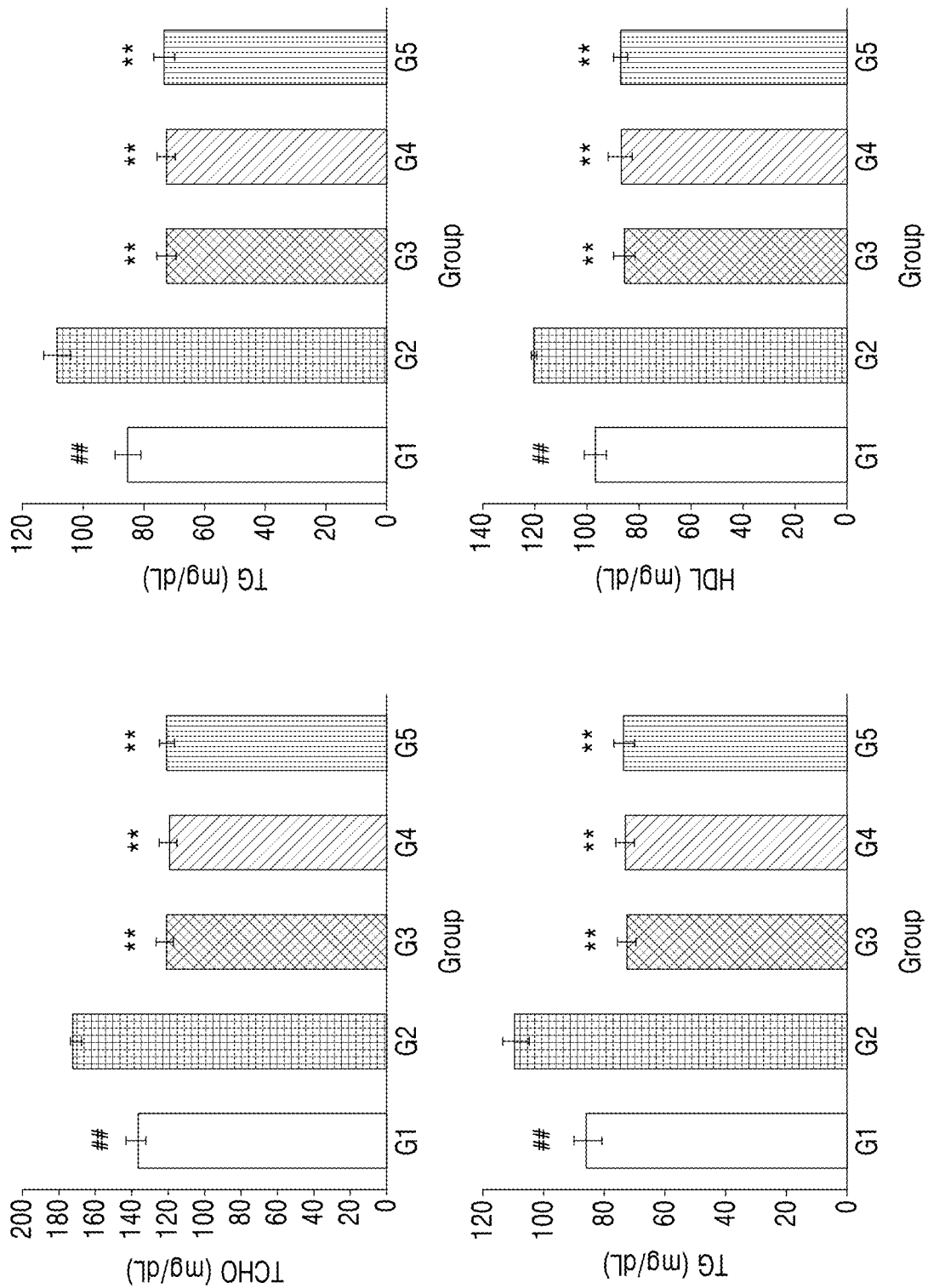
FIG. 2 shows effects of an extract of a newly selected soybean cultivar on levels of blood lipid components in an animal model having alcoholic liver injury, wherein the liver is injured by alcohol or a mixture thereof.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

A first aspect of the present disclosure provides a seed of soybean *Glycine max* (L.) Merrill cultivar SCEL-1, a plant body of the seed and a part of the plant body, and a progeny of the plant body, wherein the seed contains cyanidin-3-O-glucoside, procyanidin B2, and epicatechin, wherein an amount of the procyanidin B2 is greater than that of the cyanidin-3-O-glucoside, and a representative sample of the seed is deposited with the Korean Agricultural Culture Collection (KACC), which is an International Depository Authority (IDA) under the Budapest Treaty on the International Recognition of the Deposit of Microorganisms for the Purpose of Patent Procedure under the accession number KACC 88002BP on Nov. 8, 2018.

The term "amount" as used herein may be calculated based on an extract obtained by pulverizing the seed and incubating the pulverized seed at a temperature in a range of about 25° C. to about 55° C. for 6 hours by using 70 (v/v) % aqueous ethanol. The term "amount" as used herein is described by way of example, and should be understood as being variable depending on soil, climate conditions, and an individual seed that are considered for production of a plant body of a seed.

In the seed of the present disclosure, cyanidin-3-O-glucoside and procyanidin B2 may be contained at a ratio of 1:2.0 or more, 1:2.0 to 1:5.0, 1:2.0 to 1:3.0, 1:2.0 to 1:2.5, or 1:2.0 to 1:2.1, on a weight basis.

In the seed of the present disclosure, a total amount of procyanidin B2 and epicatechin may be, on a weight basis, twice or more or 2.5 times or more, for example, 2.6 times to 5.1 times greater than a weight of a cultivar named Wonheug.

In the seed of the present disclosure, a total amount of procyanidin B2 and epicatechin may be, on a weight basis, in a range of about 0.20% to about 0.36%.

In the seed of the present disclosure, a total amount of procyanidin B2 and epicatechin may be in a range of about 1.31% to about 2.4% based on a total weight of an extract.

In the seed of the present disclosure, a total amount of cyanidin-3-O-glucoside, procyanidin B2, and epicatechin may be in a range of about 2.1% to about 3.4% based on a total weight of an extract.

In the seed of the present disclosure, cyanidin-3-O-glucoside, procyanidin B2, and epicatechin may be contained at a ratio of 1:2.0 to 2.1:0.43 to 0.48 on a weight basis.

When the seed of the present disclosure germinates and forms a plant body, such a plant body may have characteristics listed in Table 1. Unless otherwise described in the specification, the characteristics of the soybean cultivar may be measured and verified according to "The guidelines for investigation of characteristics of each crop for examination of new varieties: Soybean *Glycine max* (L.) Merrill (Korea Seed Variety Service (KSVS) of the Ministry of Agriculture, Food and Rural Affairs (MAFRA), 2014: http.//www.seed-.go.kr)", wherein the guidelines determine matters necessary to explain the characteristics of the varieties for each crop in Annex 1 in Article 2 of the Seed Management Guidelines pursuant to Article 30 of the Act of Protection of New Varieties of Plants and Article 33 of the Enforcement Decree of the same Act, and the directions for the qualification tests necessary for cultivation examination according to Article 47 of Enforcement Regulation of the same Act. In addition, unless otherwise described herein, quantitative traits among the characteristics of the soybean cultivar are represented as mean values.

A second aspect of the present disclosure provides a plant body obtained from the seed and a part of the plant body. The part of the plant body may include pollen, a root, a seed coat, cells, a leaf, a stem, an anther, an ovule, a bean sprout, a bean pod, or an extract of any of the foregoing.

A third aspect of the present disclosure provides a progeny of the plant body.

A fourth aspect of the present disclosure provides a soybean plant body obtained by transforming the plant body of the seed or the part of the plant body, a seed from which the soybean plant is obtained, and a progeny of the soybean plant.

A fifth aspect of the present disclosure provides a product of a plant body of a seed or a part of the plant body, the method including obtaining a plant body of a soybean cultivar seed or a part of the plant body; and producing a product of the plant body or the part thereof, wherein the soybean cultivar seed is a seed of soybean *Glycine max* (L.) Merrill cultivar SCEL-1, the seed containing cyanidin-3-O-glucoside, procyanidin B2, and epicatechin, wherein an amount of the procyanidin B2 is greater than that of the cyanidin-3-O-glucoside, and a representative sample of the seed is deposited with the Korean Agricultural Culture Collection (KACC), which is an International Depository Authority (IDA) under the Budapest Treaty on the International Recognition of the Deposit of Microorganisms for the Purpose of Patent Procedure under the accession number KACC 88002BP on Nov. 8, 2018.

In one embodiment, the soybean cultivar seed in the obtaining of the plant body of the soybean cultivar seed or the part of the plant body is the same as described above. The obtaining of the plant body of the soybean cultivar seed or the part of the plant body may include germinating or growing the soybean cultivar seed, wherein the growing may include both soil cultivation and hydroponic cultivation. The obtaining of the plant body or the part thereof may also include cutting or pulverizing the plant body or the part thereof. When the part of the plant body is a seed, the seed may be pulverized or peeled.

The producing of the product of the plant body or the part thereof may vary depending on a product to be selected. When the product is an extract, the producing may include performing an extraction process on the plant body or the part thereof. When the product is oil, the producing may include performing an oil-squeezing process, such as compression. The product may include a protein concentrate, a protein isolate, a soybean hull, meal, flour, oil, an extract, or a bean sprout.

A sixth aspect of the present disclosure provides a composition for antioxidation, protection of hepatocytes, or reduction of amounts of total cholesterol, high-density lipoproteins (HDLs), low-density lipoproteins (LDLs), and triglycerides (TGs), the composition including, as an active ingredient, an extract obtained by performing an extraction process on a soybean cultivar seed by using water, $C_1$-$C_6$ alcohol, or a mixture thereof, wherein the soybean cultivar seed is a seed of soybean *Glycine max* (L.) Merrill cultivar SCEL-1, the seed containing cyanidin-3-O-glucoside, procyanidin B2, and epicatechin, or a physiologically acceptable salt of any of the foregoing, wherein an amount of the procyanidin B2 is greater than that of the cyanidin-3-O-glucoside, and a representative sample of the seed is deposited with the Korean Agricultural Culture Collection (KACC), which is an International Depository Authority (IDA) under the Budapest Treaty on the International Recognition of the Deposit of Microorganisms for the Purpose of Patent Procedure under the accession number KACC 88002BP on Nov. 8, 2018.

In the composition of the present disclosure, a total amount of procyanidin B2 and epicatechin in the extract may be in a range of about 1.31% to about 2.40% on a weight basis.

In the composition of the present disclosure, cyanidin-3-O-glucoside, procyanidin B2, and epicatechin may be included in the extract at a ratio of 1:2.0 to about 2.1:0.43 to about 0.48 on a weight basis. In addition, a total amount of cyanidin-3-O-glucoside, procyanidin B2, and epicatechin in the extract may be in a range of about 2.1% to about 3.4% on a weight basis.

In the composition of the present disclosure, an amount of the extract may be in a range of about 0.001% to about 99.9%, about 0.01% to about 80.0%, about 0.01% to about 60.0%, about 0.01% to about 50.0%, about 0.01% to about 30.0%, about 0.01% to about 20.0%, about 0.01% to about 15.0%, about 0.01% to about 10.0%, about 0.01% to about 5.0%, about 0.1% to about 99.9%, about 1.0% to about 80.0%, about 5.0% to about 60.0%, about 5.0% to about 50.0%, about 5.0% to about 30.0%, about 30.0% to about 50.0%, about 40.0% to about 80.0%, about 15.0% to about 70.0%, or about 50.0% to about 90.0%, based on a total weight of the composition.

A seventh aspect of the present disclosure provides a composition for antioxidation or protection of hepatocytes, the composition including, as an active ingredient, cyanidin-3-O-glucoside, procyanidin B2, and epicatechin, or a physiologically acceptable salt of any of the foregoing, wherein cyanidin-3-O-glucoside or a physiologically acceptable salt thereof, procyanidin B2 or a physiologically acceptable salt thereof, and epicatechin or a physiologically acceptable salt thereof are contained at a ratio of 1:2.0 to 2.1:0.43 to 0.46 on a weight basis.

In the composition of the present disclosure, an amount of each of cyanidin-3-O-glucoside or a physiologically acceptable salt thereof, procyanidin B2 or a physiologically acceptable salt thereof, and epicatechin or a physiologically acceptable salt thereof may be in a range of about 0.001% to about 99.9%, about 0.005% to about 95%, about 0.01% to about 80.0%, about 0.01% to about 60.0%, about 0.01% to about 50.0%, about 0.01% to about 30.0%, about 0.01% to about 20.0%, about 0.01% to about 15.0%, about 0.01% to about 10.0%, about 0.01% to about 5.0%, about 0.05% to about 85%, about 0.1% to about 99.9%, about 0.1% to about 80%, about 0.5% to about 75%, about 1.0% to about 80.0%, about 1% to about 70%, about 1% to about 50%, about 1% to about 30%, about 1% to about 15%, about 3% to about 15%, about 5% to about 15%, about 5% to about 65%, about 5.0% to about 60.0%, about 5.0% to about 50.0%, about 5.0% to about 30.0%, about 10% to about 60%, about 15% to about 55%, about 20% to about 50%, about 25% to about 45%, or about 30% to about 40%, about 30.0% to about 50.0%, about 40.0% to about 80.0%, about 15.0% to about 70.0%, or about 50.0% to about 90.0%, based on a total weight of the composition, respectively.

The composition of each of the sixth aspect and the seventh aspect of the present disclosure may be food, a cosmetic composition, or a pharmaceutical composition.

In the sixth aspect and the seventh aspect of the present disclosure, the expression "a physiologically acceptable salt" may include "a pharmaceutically acceptable salt". The expression "pharmaceutically acceptable" refers to possible use on animals, more particularly, to humans, without having significant toxic effects when used in a typical medicinal dosage. This expression infers that, for example, one that can be or is approved by a government or regulatory organization equivalent thereto, or one that is listed in the pharmacopoeia or recognized in other general pharmacopoeias.

In the sixth aspect and the seventh aspect of the present disclosure, the term "pharmaceutically acceptable salt" refers to a salt according to an embodiment of the present disclosure being pharmaceutically acceptable and having pharmacological activity of a parent compound. Such a salt may include:

(1) an acid addition salt formed of an inorganic acid, such as hydrochloric acid, hydrobromic acid, sulfuric acid, nitric acid, phosphoric acid, or the like; or an organic acid, such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-en-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid, muconic acid, or the like; or (2) a salt formed by substitution of an acidic proton in a parent compound.

In the sixth aspect and the seventh aspect of the present disclosure, the term "active ingredient" refers to an ingredient which exhibits a desired activity alone or an ingredient capable of exhibiting activity with a carrier that is not active by itself.

In the sixth aspect and the seventh aspect of the present disclosure, the expression "protection of hepatocytes" refers to any protection for a healthy liver or damaged liver by protecting hepatocytes from death or protecting hepatocytes from oxidative stress.

Regarding the composition for the protection of hepatocytes according to an aspect of the present disclosure, the composition may be used for preventing or treating a liver disease, wherein the liver disease may include an alcoholic liver disease caused by alcohol or a mixture thereof. The composition of the present disclosure may be able to prevent or treat a disease related to the liver or a disease occurring in the liver. In detail, the expression "prevent or treat a liver disease" as used herein refers to protection against the death of hepatocytes caused by tert-butylhydroperoxide or recovery of a liver damaged by reactive oxygen species (ROS). The term "alcoholic liver disease caused by alcohol or a mixture thereof" as used herein may include a disease resulting from liver damaged by alcohol or a mixture thereof.

In the sixth aspect and the seventh aspect of the present disclosure, the use of the composition for antioxidation may include protection of the skin from oxidative stress.

In the sixth aspect and the seventh aspect of the present disclosure, the use of the composition for reduction of amounts of total cholesterol, high-density lipoproteins (HDLs), low-density lipoproteins (LDLs), and triglycerides (TGs) may include reduction of levels of total cholesterol, HDLs, LDLs, and TGs in the blood. The use of the composition for reduction of amounts of total cholesterol, HDLs, LDLs, and TGs may be derived from a tissue, wherein the tissue may be a liver tissue or an adipose tissue. Thus, the composition may be used to prevent or treat a disease involving symptoms that increase the amounts of total cholesterol, HDLs, LDLs, and TGs in the blood, wherein the disease may be, for example, obesity or diabetes.

In the seventh aspect of the present disclosure, the composition may include, as an active ingredient, an extract obtained by performing an extraction process on a soybean cultivar seed by using water, $C_1$-$C_6$ alcohol, or a mixture thereof, wherein a representative sample of the soybean cultivar seed is deposited with the Korean Agricultural Culture Collection (KACC), which is an International Depository Authority (IDA) under the Budapest Treaty on the International Recognition of the Deposit of Microorganisms for the Purpose of Patent Procedure under the accession number KACC 88002BP on Nov. 8, 2018.

In one embodiment, the composition may be a pharmaceutical composition effective in treating a liver disease, and more particularly, may be a pharmaceutical composition effective in treating a liver disease caused by oxidative stress.

When the composition of the present disclosure is applied to medicines, the composition may be formulated into an agent in a solid, semi-solid, or liquid form for oral or parenteral administration by adding a commonly used inorganic or organic carrier thereto which includes the composition as an active ingredient.

Examples of the agent for oral administration may include tablets, pills, granules, capsules, powders, infinitesimal grains, emulsions, syrup, pellets, and the like. In addition, examples of the agent for parenteral administration may include injections, instillations, ointments, lotions, sprays, suspensions, emulsions, suppositories, and the like. To formulate the active ingredient of the present disclosure, the active ingredient may be easily formulated according to the conventional method, and a surfactant, an excipient, a coloring agent, a flavoring agent, a preservative, a stabilizer, a buffer, a suspension, and other common adjuvants may be used as appropriate.

The composition according to the present disclosure may be administered orally, parenterally, rectally, topically, transdermally, intravenously, intramuscularly, intraperitoneally, subcutaneously, and the like.

In addition, a dosage of the active ingredient may vary depending on the age, gender, and weight of a subject to be treated, a particular disease or pathological condition to be treated, the severity of a disease or pathological condition, a route of administration, and a determination made by a prescriber. The determination of the dosage based on these factors may be within a level of one of ordinary skill in the art, and the dosage may be in a range of about 0.001 mg/day to about 2,000 mg/kg/day, more particularly, a range about 0.5 mg/kg/day to about 1,500 mg/kg/day.

Regarding the composition for the protection of the liver according to an aspect of the present disclosure, the composition may include a health food composition.

In one embodiment, the composition may be processed into a drink, fermented milk, a cheese, a yogurt, a juice, a probiotic agent, and a health supplement, each including the composition. In addition, the composition may be used in a variety of other food additives.

In one or more embodiments, the composition may contain other components that exhibit a synergistic effect with main effects within a range that does not damage the intended main effects of the present disclosure. For example, to improve physical properties, the composition may further include an additive, such as a flavoring agent, a dye, a bactericide, an antioxidant, a preservative, a moisturizer, an instillation, an inorganic salt, an emulsifier, or a synthetic polymer. In addition, the composition may further include an adjuvant component, such as a water-soluble vitamin, an oil-soluble vitamin, a polymeric peptide, a polymeric polysaccharide, or a seaweed extract. The components above may be appropriately selected and mixed by one of ordinary skill in the art without difficulty depending on the formulation and purpose of use, and an amount of the components to be added may be selected within a range that does not damage the objects and effects of the present disclosure.

The composition of the present disclosure may be in various forms, such as a solution, an emulsion, a viscous mixture, a tablet, a powder, and the like, and may be administered by various methods using a simple drink, an injection, a spray, or a squeezer.

The composition may include a cosmetic composition, and may be formulated in a parenteral dosage form. An example of the parenteral dosage form may include an injection or an external skin application, and examples of the external skin application may include a cream, gel, ointment, skin emulsifier, skin suspension, transdermal delivery patch, drug-containing bandage, lotion, or any combination thereof.

In the external skin application, components such as typical cosmetics or medicines used for external skin applications, for example, an aqueous component, an oily component, a powder component, an alcohol component, a moisturizer, a thickener, an ultraviolet absorber, a whitening agent, an antiseptic, an antioxidant, a surfactant, a flavoring agent, a dye, various skin nutrients, or any combination thereof, may be appropriately mixed as needed.

In the external skin application, a chelating agent such as disodium edentate, trisodium edentate, sodium citrate, sodium polyphosphate, sodium metaphosphate, gluconic acid, and the like; caffeine, tannin, verapamil, licorice extract, glabridin, hot water extract of calines from fruit, and various herb medicines; medicines such as tocopherol acetate, glycyrrhizic acid, tranexamic acid, or a derivative or salt of any of the foregoing; vitamin C, ascorbic acid magnesium phosphate, ascorbic acid glucoside, arbutin, and kojic acid; and sugars such as glucose, fructose, and trehalose, may be mixed as appropriate.

In the composition of the present disclosure, the extract may be obtained according to the method including contacting the seed with water, $C_1$-$C_6$ alcohol, or a mixture thereof. The contacting may include incubating a mixture which is obtained by mixing the seed with water, $C_1$-$C_6$ alcohol, or a mixture thereof, and the incubating may be performed under heat or pressure. The incubating may be also performed under stirring, and may be performed at a temperature in a range of room temperature to a reflux temperature, for example, room temperature to about 100° C., room temperature to about 80° C., room temperature to about 70° C., about 50° C. to about 70° C., about 40° C. to about 100° C., about 40° C. to about 80° C., about 40° C. to about 60° C., or at a temperature of about 50° C. The incubating may be performed under microwave irradiation. The alcohol used herein may include methanol, ethanol, propanol, butanol, pentanol, hexanol, or a mixture thereof. The alcohol used herein may be a solution at a concentration in a range of about 30 volume % to about 100 volume %, about 30 volume % to about 90 volume %, about 30 volume % to about 80 volume %, about 40 volume % to about 80 volume %, about 50 volume % to about 100 volume %, about 50 volume % to about 90 volume %, about 50 volume % to about 80 volume %, or about 60 volume % to about 100 volume %.

A volume of a solvent used in the extraction process may be about 2 times to about 15 times, about 3 times to about 15 times, about 4 times to about 15 times, about 5 times to about 15 times, or about 10 times greater than the soybean. The extraction process may include heat extraction, cold extraction, reflux cooling extraction, or ultrasonic extraction, and there is no limitation as long as the extraction process is obvious to one of ordinary skill in the art. The time for which the extraction process is performed may be in a range of about 2 hours to about 8 hours, about 4 hours to about 8 hours, about 5 hours to about 7 hours, about 5.5 hours to about 6.5 hours, or may be about 6 hours. The temperature may vary depending on conditions including a solvent used for the extraction process. To obtain a greater amount of active ingredients, the extraction process may be performed one or more times. For example, an extract obtained by combining all the extracts from the extraction process performed one to 5 times, one to 4 times, or 3 times consecutively may be used.

The extract of the soybean cultivar SCEL-1 of the present disclosure may include a crude extract of the soybean cultivar SCEL-1, and may be contained as a water-soluble fraction of the organic solvent obtained by further extraction performed on the crude extract.

Examples of the organic solvent may include hexane, methylene chloride, ethyl acetate, n-butanol, and the like. According to the method of the present disclosure, the extract or the water-soluble fraction thereof may be used as it is. In one embodiment, the extract may be used as a concentrate obtained by concentration, and in one or more embodiments, the extract may be used in a lyophilized form obtained by concentration followed by lyophilization.

An eighth aspect of the present disclosure provides a method of preventing or reducing oxidation in a subject, protecting hepatocytes, or reducing a level of at least one of total cholesterol, HDLs, LDLs, and TGs, the method including administrating the composition of the sixth or seventh aspect of the present disclosure to a subject.

The administrating may be oral or parenteral administration. The method of the present disclosure may be used to increase a survival rate of hepatocytes in a subject or to prevent or treat an alcoholic liver disease. In addition, the method of the present disclosure may be used to reduce a level of at least one of total cholesterol, HDLs, LDLs, and TGs in the blood. In addition, the method of the present disclosure may be used to prevent or treat obesity or diabetes.

The method of the present disclosure may include administrating the composition to the skin of a subject. Here, the administrating may include coating or applying the composition to the skin. The method of the present disclosure may be considered as a make-up method, and may prevent or reduce the occurrence of ROS in the skin. The ROS may be produced when ultraviolet rays are irradiated to the skin.

The subject may include a mammal, for example, a cow, a pig, a cat, a dog, or a sheep. That is, the subject may be a mammal other than a human.

Hereinafter, the present disclosure will be described in detail with reference to the following Examples. However, these Examples are for illustrative purposes only, and the scope of the present disclosure is not intended to be limited thereby.

Examples 1: Breeding and Characteristics of New Cultivar

1. Breeding of Cultivar 20 soybean seed grains, which are black flat-shaped granules collected as genetic resources from Idong-eup, Yongin-si, Gyeonggi-do, Korea, were prepared. As a result of cultivating the soybean seeds, separation occurred in terms of shape and color of the flowers, and in this regard, it was confirmed that the traits of the soybean seeds were not fixed. For example, the flower color appeared separately as white or pink. In this regard, the traits of the soybean seeds did not seem to be fixed, and thus, the soybean seeds were not recognized as species due to lack of stability and uniformity.

Therefore, the inventors of the present disclosure bred a cultivar by using the soybean seeds according to a pure line selection breeding method. The pure line selection was carried out from 2013 to 2017, and more particularly, it was carried out by the whole crop experimental field in the Rural Development Administration (RDA): National Institute of Crop Science (NICS) located in Suwon, Republic of Korea from 2013 to 2014, and then, in the field located in Iseomyeon, Wanju-gun, Republic of Korea from 2015 to 2017.

A specific process of the pure line selection from the collected genetic resources of the soybean is as follows: as genetic resources, 20 soybean seeds were shown at the beginning of June every year from 2013 to 2016 in the experimental field affiliated with the RDA; then, 1 seed was selected for the purity improvement at the end of November and then harvested as a sowing seed for the following year. After four years of the pure line selection process, one finally fixed pure line seed was selected.

Figure 4:
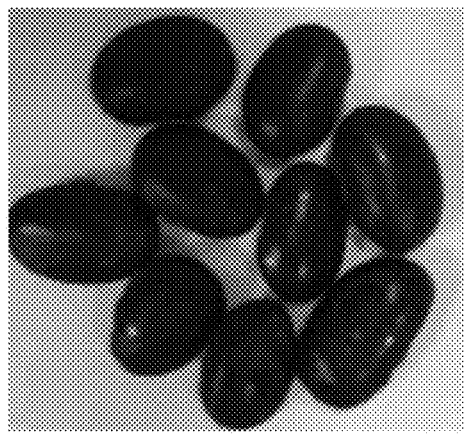
FIG. 4 is a photograph of seeds of selected soybean cultivar SCEL-1.

To confirm uniformity, traits, such as hypocotyl color, flower color, trichome color, legume color, leaf shape, growth type, flowering periods, and maturity, were examined every year. In the pure line separation process performed on the collected genetic resources, separation was observed in the hypocotyls color and the flower color in 2013, whereas no separation was observed with respect to the other traits. In addition, the progeny selected in 2013 was found to maintain uniformity in target traits among traits examined from 2014 to 2017. The distinguishable features between a standard cultivar (named Wonheug) and a control cultivar (named Cheongja-3) are clearly shown in Table 1 in terms of growth type, days to flowering, hypocotyl color, weight of 100 beans, and leaf shape. Table 1 shows the characteristics of the finally selected pure line. In Table 1, the finally selected line (cultivar) was named SCEL-1. FIG. 4 is a photograph of seeds of the finally selected cultivar SCEL-1.

TABLE 1

| Source | Growth type (Determinate, Indeterminate) | Number of days to flowering | Flower color (violet or white) | Hypocotyl color (violet or green) | Trichome color (brown, light gray) | Testa | Hilum color | 100-seed weight (g) | Leaf shape |
|---|---|---|---|---|---|---|---|---|---|
| Wonheug (standard) | Determinate | 66 | Violet | Violet | Brown | Black | Black | 11.6 | Globular |
| Cheongja-3 (control) | Determinate | 70 | Violet | Violet | Brown | Black | Black | 40.7 | Globular |

TABLE 1-continued

| Source | Growth type (Determinate, Indeterminate) | Number of days to flowering | Flower color (violet or white) | Hypocotyl color (violet or green) | Trichome color (brown, light gray) | Testa | Hilum color | 100-seed weight (g) | Leaf shape |
|---|---|---|---|---|---|---|---|---|---|
| Selected cultivar (SCEL-1) | Indeterminate | 58 | White | Green | Brown | Black | Black | 8.8 | Oblique ellipse |

2. Identification of Cultivar Characteristics Relative to Control Cultivar

To compare the agricultural performance of the finally selected pure line cultivar SCEL-1 relative to the existing cultivars, the performance of each cultivar was identified by repeating the randomized block design three times by using the Wonheug bean as a standard cultivar and Cheongja-3 as a control cultivar in the field affiliated with the NISC in summer of 2017. Here, the agronomic traits of each cultivar were examined by cultivating seeds plants after sowing two seeds per hole (60 cm×15 cm) containing four rows (4 meters long) in an experimental plot on Jun. 8, 2017, and then cultivating the seeds. The Wonheug bean (Cultivar Application Publication Number: 2010-341) is a microcarpa bean cultivar with a black seed coat developed by the NICS in 2009, and is currently the most cultivated cultivar in farming. The Wonheug bean is similar to the selected cultivar SCEL-1, and thus, may be used as a standard cultivar for the comparison. The control cultivar, Cheongja-3 (Cultivar Application Publication Number: 2005-176), was developed by the NICS in 2004 and is a soybean cultivar that has a black seed coat, is large-sized, and is used for cooking with rice. The Wonheug bean and Cheongja-3 are commercially available from the Korean Seed and Variety Service (KSVS) or the like.

The agronomic traits and traits examined for the performance testing were examined mainly in terms of yield component traits, such as stem length, number of nodes, number of branches, and the like. To examine such yield component traits, 10 plants within each experimental plot were examined during a maturation period in terms of stem length, number of nodes, number of branches, number of pods, 100-seed weight, yield per plant, yield per area, and yield per 10 are(a).

Tables 2 and 3 show the characteristics of the selected soybean cultivar, the standard cultivar, and the control cultivar.

TABLE 2

| Source | Stem length (cm) | Number of nodes | Number of branches | Seed number per pod | | |
|---|---|---|---|---|---|---|
| | | | | 1 pod | 2 pods | 3 pods |
| Wonheug (standard) | 56.6 ± 04.3 | 14.7 ± 1.7 | 6.7 ± 2.1 | 18.8 ± 2.3 | 201 ± 21 | 32 ± 15.2 |
| Cheongja-3 (control) | 71.9 ± 2.7 | 14.1 ± 0.3 | 7.3 ± 0.6 | 13.8 ± 4.9 | 81 ± 12 | 4.7 ± 0.8 |
| Selected cultivar (SCEL-1) | 82.9 ± 1.4 | 15.8 ± 0.5 | 6.4 ± 0.3 | 12.9 ± 2.3 | 133 ± 44 | 38.3 ± 8.6 |

TABLE 3

| Source | Total number of pods | Number of grains | 100-seed weight (g) | Yield per plant (g) | Yield per area (kg) | Yield per 10 are (a) (kg) |
|---|---|---|---|---|---|---|
| Wonheug (standard) | 252 ± 31 | 512 ± 70 | 11.6 ± 0.2 | 32.9 ± 3.3 | 6.6 ± 0.7 | 587 ± 60 |
| Cheongja-3 (control) | 100 ± 12 | 191 ± 25 | 40.7 ± 3.1 | 26.7 ± 3.2 | 5.3 ± 0.6 | 477 ± 57 |
| Selected cultivar (SCEL-1) | 184 ± 54 | 397 ± 113 | 9.4 ± 0.4 | 23.1 ± 2.0 | 4.6 ± 0.4 | 413 ± 36 |

Referring to Tables 2 and 3, it was found from the examination that the selected cultivar was longer than the standard cultivar, Wonheug, by 26 cm, and had one more node than the standard cultivar, Wonheug. In addition, regarding the number of branches, it was found from the examination that the selected cultivar was had about 6.4 branches similar to the standard cultivar, and regarding the number of pods, the constitution ratio of the 1-pod, 2-pods, and 3-pods was similar to the standard cultivar. Regarding the total number of pods, the number of grains, the yield per plant, and the yield per area, which indicate the yield component traits, the selected cultivar had 184 pods, 397 grains, 23.1 g of the yield per plant, and 4.6 g of the yield per area, wherein the resulting numbers and yields were lower than those of the standard cultivar. Here, 100 grains were weighed at 9.4 g, and in this regard, the selected cultivar had small grains as compared with the standard cultivar. When the yield per 10a was calculated based on the results above, the selected cultivar showed 413 kg/10 a, which was only about 70% of the yield per 10a of the standard cultivar, Wonheug. However, the amounts of procyanidin B2 and epicatechin, which are functional substances, were about 301% and 217%, respectively, in powder having a dry weight. In detail, the amount of procyanidin B2 was 149.4 ug/100 mg, 49.5 ug/100 mg, and 34.3 ug/100 mg in the selected cultivar SCEL-1, Wonheug, and Cheongja-3, respectively. The amount of epicatechin was 46.9 ug/100 mg, 21.6 ug/100 mg, and 20.1 ug/100 mg in the selected cultivar SCEL-1, Wonheug, and Cheongja-3, respectively. Here, the amounts of procyanidin B2 and epicatechin were confirmed by an extraction process performed according to the method of Section 1 in Example 2.

According to the experiments, the cultivar SCEL-1 was found to have high uniformity and was distinguished from the standard cultivar and the existing cultivars by the comparison, and was also able to be recognized as an independent cultivar with distinct characteristics in terms of the agronomic traits, the yield ability, and the functional material contents.

This newly selected cultivar of a black small-sized bean having an oblique ellipse shape was named SCEL-1, and was deposited with the Korean Agricultural Culture Collection (KACC), which is an International Depository Authority (IDA) under the Budapest Treaty on the International Recognition of the Deposit of Microorganisms for the Purpose of Patent Procedure under the accession number KACC 88002BP on Nov. 8, 2018.

FIG. 1 shows a schematic breeding diagram of a soybean cultivar according to the present disclosure.

Example 2: Extract Obtained by Performing an Extraction Process on a Newly Selected Soybean Seed by Using Water, Alcohol, or a Mixture, and Use of the Extract In this Example, an extract was prepared from a seed of the newly selected soybean cultivar SCEL-1 of Example 1, and an effect of the extract was identified.

1. Preparation of an Extract

Immediately before analyzing a seed of the selected cultivar, the seed was pulverized by using a high-speed pulverizer (Wonder Blender, 820 W, 30000 RPM, Sanplatec Corp) to prepare powdered seed. 1 g of the powdered seed thus obtained was mixed with 100 ml of 70 (v/v) % aqueous ethanol in a glass tube, and the mixed solution was stirred at a temperature of 50° C. for 6 hours by using a magnetic bar. Then, the resulting extract was filtered through filter paper (Grade No. 131 Qualitative filter paper, Advantec).

Afterwards, the ethanol layer was dried in a nitrogen gas drier (hurricane-Eagle, Chongmin Technology) for 1 hour, and then, was lyophilized for one day to completely remove moisture, thereby obtaining 0.135 g (standard deviation (SD): ±0.015) of a soybean extract. In the following experiments, for use of the soybean extract, it was dissolved at a concentration of 30 mg/ml in 50% v/v aqueous ethanol.

2. Antioxidant Efficacy of Extract

An effect of the extract obtained in Section 1 on eliminating 2,2-diphenyl-1-picrylhydrazyl (DPPH) radical scavenging ability in cells, i.e., antioxidant activity, was analyzed.

Regarding the DPPH radical elimination activity, the soybean extract was added to 0.8 ml of a 0.2 mM DPPH solution in 99.9% aqueous ethanol so that a final concentration of the mixed solution became 0.0625 mg/mL, 0.125 mg/mL, 0.25 mg/mL, 0.5 mg/mL, 1.0 mg/mL, and 2.0 mg/mL, respectively, and then, the resulting solution was allowed to stand in a dark room for 30 minutes. Afterwards, by using a microplate reader (molecular device, Sunnyvale, Calif., USA), the absorbance was measured at 517 nm, and the antioxidant activity was evaluated. Here, as a control group, an extract of Wonheug having similar cultivar characteristics was used.

As a result, it was confirmed that the extract of the newly selected soybean cultivar and the extract of Wonheug each showed DPPH radical scavenging ability $IC_{50}$ values of 0.19 mg/ml and 0.33 mg/ml, respectively. That is, it was confirmed that the extract of the newly selected soybean cultivar showed high antioxidant activity as compared with the extract of Wonheug. Here, the DPPH radical scavenging ability was calculated according to the following equation.

DPPH radical scavenging ability=[1−$As/Abk$]×100
(wherein $As$ and $Abk$ each indicate absorbance of each sample and blank)

Then, based on the $IC_{50}$ values, a calibration curve was set at the concentrations of 0.0625 mg/mL, 0.125 mg/mL, 0.25 mg/mL, 0.5 mg/mL, 1.0 mg/mL, and 2.0 mg/mL used above, so as to calculate and represent concentrations at 50% of the maximal scavenging ability.

3. Determination of Efficacy of the Soybean Extract to Prevent or Treat an Alcoholic Liver Disease The efficacy of the soybean extract on an alcoholic liver disease in a rat model having alcoholic liver injury was examined, wherein the soybean extract was caused by alcohol or a mixture thereof.

In detail, 5-week-old rats (Spargue-Dawley rats) (male, weight at the time of obtainment: 18.84 g to 21.17 g, weight at the time of initiation of administration: 21.73 g to 24.23 g, OrientBio) were freely fed for 1 week, and then, were fed with liquid food containing alcohol or the extract of the newly selected soybean cultivar for 21 days as follows, thereby comparing the degree of liver damage. To compare the degree of liver damage, amounts of blood lipids, cholesterol, HDL, and LDL were measured by using a TG cholesterol assay kit (TG assay kit/cholesterol assay kit Abcam). Here, the blood was centrifuged at a speed of 2,580×g for 10 minutes, and only the supernatant was used for the analysis. In addition, after the rats were sacrificed, liver tissues were collected therefrom, and stained with hematoxylin-eosin and oil red, so as to measure a ratio of a hepatic steatosis region and a mean diameter of hepatocytes. In detail, liver tissue was removed on the date of the autopsy, and then, fixed in a 10% neutral buffered formalin solution.

The fixed tissue was fixed again in a 10% neutral buffered formalin solution for 24 hours, so as to prepare a paraffin block. Here, a slide was prepared to have a thickness of about 3 μm, and then, a staining process was performed on a tissue.

① Group 1: Control, intake of liquid food only
② Group 2: Ethanol intake group
③ Group 3: Administration of ethanol+25 mg/kg/day of extract of selected new soybean cultivar named SCEL-1
④ Group 4: Administration of ethanol+100 mg/kg/day of extract of selected new soybean cultivar named SCEL-1
⑤ Group 5: Administration of ethanol+100 mg/kg/day of silymarin extract (Sigma Aldrich, Silymarin flavonolignans, Mixture of anti-hepatotoxic flavonolignans from the fruit of *Silybum marianum*)

FIG. 2 shows effects of an extract of the newly selected soybean cultivar on levels of blood liquid components in an animal model having alcoholic liver injury. As shown in FIG. 2, the extract of the newly selected soybean cultivar significantly reduced the total amounts of cholesterol, TGs, HDLs, and LDLs. In FIG. 2, TCHO indicates total cholesterol, TG indicates triglyceride, HDL indicates high-density lipoprotein, and LDL indicates low-density lipoprotein.

Figure 3:
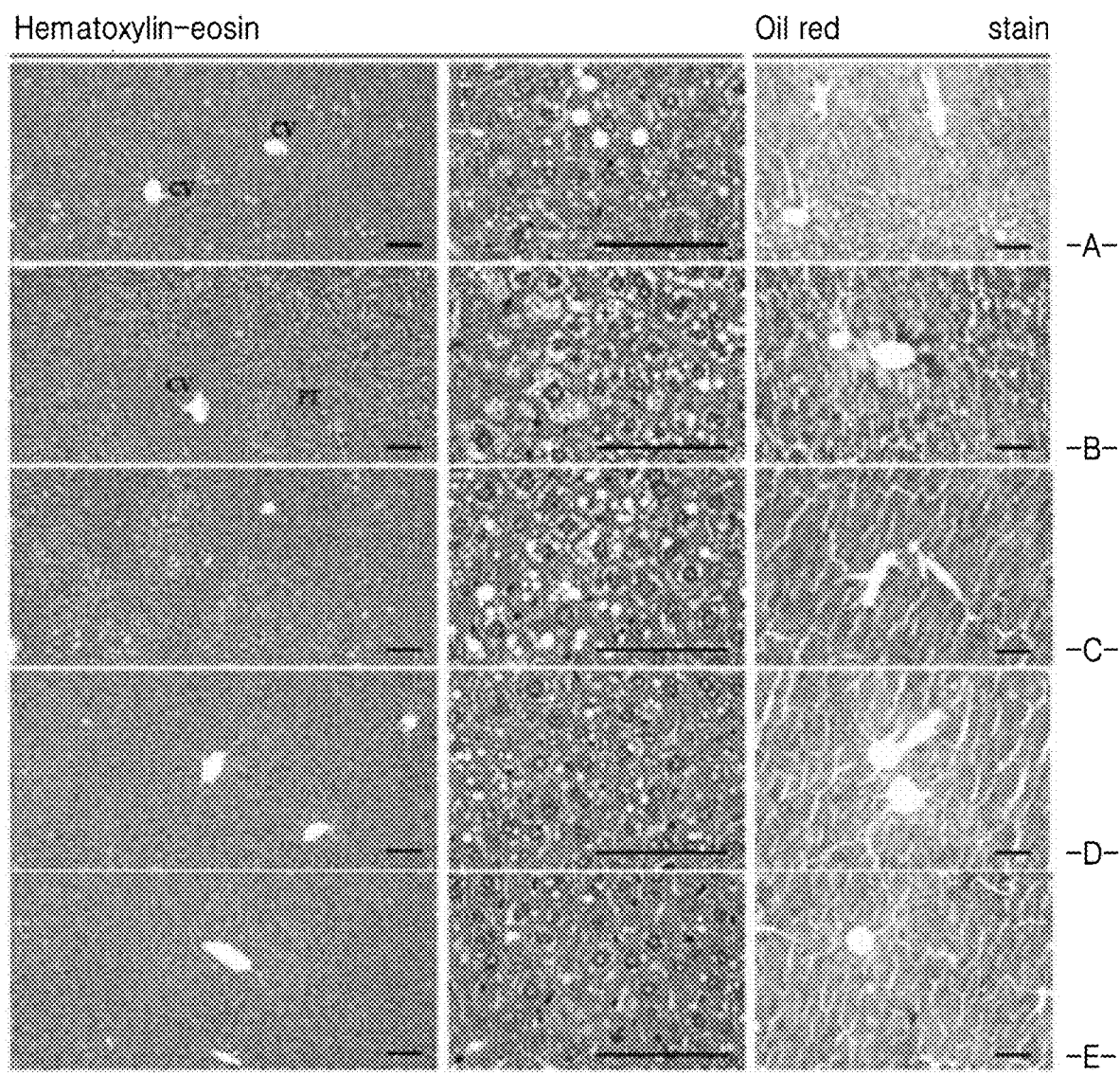
FIG. 3 shows effects of an extract of a newly selected soybean cultivar on liver tissue in an animal model having alcoholic liver injury, wherein the liver is injured by alcohol or a mixture thereof.

FIG. 3 shows effects of an extract of the newly selected soybean cultivar on a liver tissue in an animal model having alcoholic liver injury. In FIG. 3, Hematoxylin-eoxin indicates a liver tissue stained with hematoxylin-eoxin, and Oil red indicates a liver tissue stained with oil red. A, B, C, D, and E in FIG. 3 refer to Groups 1, 2, 3, 4, and 5, respectively, and CV and PT each indicate a central vein and a portal triad area, respectively.

As shown in FIG. 3, in the liver tissue of the alcohol-induced group, histological changes were observed in relation to the distribution of large fats, as compared with the liver tissue of the normal group. Such histological changes or fat distribution were still observed in the group to which 25 mg/kg/day of the SCEL-1 extract was administered (see FIG. 3C). However, in the group to which 100 mg/kg/day of the SCEL-1 extract was administrated (see FIG. 3D) or the group to which 100 mg/kg/day of the silymarin extract was administered (see FIG. 3E), the hepatic steatosis regions were found to be reduced and the occurrence of histological changes in the liver was efficiently prevented. As shown in Table 4, the size of the hepatic lesion sites and the diameter of the hepatocytes according to fat accumulation both showed a statistically significant decrease in the group to which 100 mg/kg/day of the SCEL-1 extract was administrated and in the group to which 100 mg/kg/day of the silymarin extract was administered.

TABLE 4

Histomorphometrical analysis of male rat

| | Hepatic steatosis region (%/mm$^2$) | diameter of hepatocyte (um) |
|---|---|---|
| G1 | 33.32 ± 1.84$^{\#\#}$ | 18.14 ± 0.25$^{\#\#}$ |
| G2 | 71.45 ± 2.58 | 25.70 ± 0.86 |
| G3 | 70.47 ± 3.83 | 25.31 ± 0.96 |
| G4 | 53.73 ± 4.38** | 22.12 ± 0.83** |
| G5 | 55.48 ± 4.24** | 21.30 ± 0.97** |

The data in Table 4 are expressed as the mean ± SD that was statistically analyzed by the LSD test method.
$^{\#\#}$Significantly different between G1 and G2, $P < 0.01$
**Significantly different from G2, $P < 0.01$
G1: Normal control group (1% Tween 80 in 1% CMC), n = 8
G2: Vehicle control group (1% Tween 80 in 1% CMC), n = 8
G3: Test group (25 mg/kg/day), n = 8
G4: Test group (100 mg/kg/day), n = 8
G5: Reference control group (silymarin 100 mg/kg/day), n = 8

Analysis of Components of Soybean Extract

The soybean extract was subjected to mass spectrometry, so as to analyze active ingredients in the soybean extract.

In detail, the analysis of components in the soybean extract was carried out by using an Agilent 1260 HPLC system and a Bruker MicrOTOF-Q II mass spectrometer. Here, for the column analysis, a Prevail C18 column (250 mm×4.6 mm, 5 um), Solvent A of a mobile phase consisting of 95% water/5% acetonitrile (0.1% formic acid), and Solvent B of a mobile phase consisting of 95% acetonitrile/5% water (0.1% formic acid) were used. Here, the flow rate of the solvent was set at 0.7 ml/min, and the concentration gradient conditions of the solvent used for the separation of components are shown in Table 5.

TABLE 5

| Time (min) | A (%) | B (%) | Flow rate (ml/min) | Maximum pressure (bar) |
|---|---|---|---|---|
| 0.00 | 95.00 | 5.00 | 0.700 | 1000.00 |
| 3.00 | 95.00 | 5.00 | 0.700 | 1000.00 |
| 23.00 | 50.00 | 50.00 | 0.700 | 1000.00 |
| 28.00 | 0.00 | 100.00 | 0.700 | 1000.00 |
| 33.00 | 0.00 | 100.00 | 0.700 | 1000.00 |
| 33.10 | 95.00 | 5.00 | 0.700 | 1000.00 |
| 40.00 | 95.00 | 5.00 | 0.700 | 1000.00 |

Here, the temperature of the column was maintained at 35° C., and 10 μL of the sample was injected into the column. A mass spectrometer was used to analyze ingredients contained in the soybean extract under conditions of mode: ESI(+); mass range: 50 m/z to 800 m/z; nebulizing gas: 8 L/min; source gas temperature: 180° C.; capillary voltage: +4,500 V; and cone voltage: 35 V.

As a result, the amount of each of epicatechin and procyanidin B2 contained in the selected cultivar named SCEL-1 was in a range of about 0.32% to about 0.46% and in a range of about 1.0% to about 2.0%, respectively, which was significantly higher than the amounts thereof in Wonheug, which were respectively in a range of about 0.14% to about 0.15% and in a range of about 0.33% to about 0.35%.

In cultivar named SCEL-1 selected on the basis of cyanidin-3-O-glucoside which is a representative substance of anthocyanin antioxidants, cyanidin-3-O-glucoside, procyanidin B2, and epicatechin were contained at a ratio of 1:2.0 to 2.1:0.43 to 0.48. Meanwhile, in Wonheug, cyanidin-3-O-glucoside, procyanidin B2, and epicatechin were contained at a ratio of 1:0.43 to 0.70:0.19 to 0.25.

According to the one or more embodiments, a seed of soybean cultivar SCEL-1, a plant body obtained from the seed or a part of the plant body, and a progeny of the plant body may be used to prepare a product.

According to the one or more embodiments, a soybean plant body obtained by transforming the plant body of the seed or the part of the plant body, a seed from which the soybean plant is obtained, and a progeny of the soybean plant may be used to prepare a product.

According to the one or more embodiments, a product may be efficiently prepared according to a method of producing a product from the plant body or the part thereof.

According to the one or more embodiments, a composition for antioxidation, protection of hepatocytes, or reduction of amounts of total cholesterol, HDLs, LDLs, and TGs may be used for antioxidation, protection of hepatocytes, or reduction of amounts of total cholesterol, HDLs, LDLs, and TGs.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of preventing or reducing oxidation in a subject, protecting hepatocytes, or reducing a level of at least one of total cholesterol, high-density lipoproteins (HDLs), low-density lipoproteins (LDLs), and triglycerides (TGs), the method comprising, administering a composition as an active ingredient, said composition comprising an extract obtained by performing an extraction process on a soybean cultivar seed by using water, $C_1$-$C_6$ alcohol, or a mixture thereof, wherein the soybean cultivar seed is a seed of soybean *Glycine max* (L.) Merrill cultivar SCEL-1, the seed containing cyanidin-3-O-glucoside, procyanidin B2, and epicatechin, wherein an amount of the procyanidin B2 is greater than that of the cyanidin-3-O-glucoside, and a representative sample of the seed is deposited with the Korean Agricultural Culture Collection(KACC), which is an International Depository Authority(IDA) under the Budapest Treaty on the International Recognition of the Deposit of Microorganisms for the Purpose of Patent Procedure under the accession number KACC 88002BP on Nov. 8, 2018.

2. The method of claim 1, wherein a total amount of procyanidin B2 and epicatechin in the extract is in a range of about 1.3% to about 2.4% on a weight basis.

3. The method of claim 1, wherein cyanidin-3-O-glucoside, procyanidin B2, and epicatechin are comprised in the composition at a ratio of 1:2.0 to 2.1:0.43 to 0.48, on a weight basis.

4. The method of claim 1, wherein an amount of the extract is in a range of about 0.005% to about 99.9% based on a total weight of the composition.

5. The method of claim 1, wherein the composition is food, a cosmetic composition, or a pharmaceutical composition.

6. The method of claim 5, wherein the method is for protecting hepatocytes from oxidative stress.

7. The composition method of claim 5, wherein the method is for protecting skin from oxidative stress.

8. The method of claim 5, wherein the method is for preventing or treating an alcoholic liver disease caused by alcohol or a mixture thereof.

* * * * *